United States Patent [19]

Ricketts

[11] Patent Number: 5,720,984
[45] Date of Patent: *Feb. 24, 1998

[54] BOVINE TEAT DIP

[75] Inventor: David J. Ricketts, Irvine, Calif.

[73] Assignee: Devtech Corporation, Irvine, Calif.

[*] Notice: The term of this patent shall not extend beyond the expiration date of Pat. No. 5,534,266.

[21] Appl. No.: 675,918

[22] Filed: Jul. 5, 1996

Related U.S. Application Data

[63] Continuation-in-part of Ser. No. 262,774, Jun. 20, 1994, Pat. No. 5,534,266.

[51] Int. Cl.$^6$ .......................... A61K 31/19; A61K 31/045
[52] U.S. Cl. .......................... 424/672; 514/571; 514/738
[58] Field of Search .......................... 424/672; 514/571, 514/738

[56] References Cited

U.S. PATENT DOCUMENTS 4,466,959  8/1984  Lauermann et al. .................. 424/150

*Primary Examiner*—Zohreh Fay
*Attorney, Agent, or Firm*—Willie Krawitz

[57] ABSTRACT

An iodophor teat dip is disclosed comprising a solution of a fatty alcohol polyglycol ether carboxylic acid, glycerin, $I_2$, I- (or HI) and, a pH buffer. The teat dip reduces the spread of mastitis infection, imparts a smoother teat condition, improves milk let down, and has few discernible long term effects.

20 Claims, No Drawings

BOVINE TEAT DIP

This application is a continuation in part of Ser. No. 08/262,774 filed Jun. 20, 1994 now U.S. Pat. No. 5,534,266.

BACKGROUND OF THE INVENTION

This invention relates to a new and improved iodophor teat dip containing $I_2$ and $I-$ (or HI), a specific surfactant, and glycerin which is suitable for reducing the spread of mastitis infection, and improving teat appearance and skin condition; this in turn enables faster let down and milk out.

Many types of teat dip similar formulations have been employed in the past, and typical examples are found in U.S. Pat. Nos. 2,977,315; 3,950,554; 4,049,830 4,258,056; 4,371, 517; 4,671,958; 4,678,668; 4,940,702; 5,028,427; 5,175, 160; 5,208,257; and, German Patent 2,936,934.

The use of $I_2$ with $I-$ (or HI) which complexes, rather than reacts with the surfactant to produce unwanted and possibly toxic reaction products, is disclosed in U.S. Pat. Nos. 2,599,140; 2,710,277 and 2,977,315 which describe tamed iodine or iodophor, etc. Also, the use of polyethenoxy detergents and $I_2$ is disclosed in an article by Benjamin Carroll in the Journal of Bacteriology, 69; 413–417, (1955). In an attempt to avoid the use of $I_2$ and $I-$ (or HI), the use of bromo-nitro-propanol as the germicide in teat dips is disclosed in U.S. Pat. No. 4,049,830, but this latter formulation is considered to have insufficient germicidal properties compared to using iodine.

Consequently, present commercial teat dip formulations have been developed with the intent of combining desired germicidal properties with suitable emolliency, and include surfactants such as 9–12 mole ethoxylated phenols containing $I_2$, $I-$ and glycerine. A surfactant of this type employed in a teat dip is sold by Norman Fox & Co. under the trade name of NORFOX N-P9, and listed in "McCutcheon's Emulsifiers and Detergents", 1989 specifically for use with iodophors. However, the NORFOX N-P9 formulation tends to cause the teat skin to become chapped, cracked and calloused, which in turn leads to infection, which can provide a mastitis site, and weaken the cow for other infections, delayed milk let down, and discomfort when milking.

Another type of teat dip is sold as Klenzade™ Teat Guard, containing a nonyl phenoxypolyethoxy ethanol surfactant having 1% titratable iodine, but this product does not keep a soft teat skin. Still other bovine teat dip formulations have employed an emollient such as lanolin, but these formulations have failed to exhibit the desired characteristics of emolliency.

A bovine teat dip formulation is desired which has a suitable capability for dispersing $I_2$ and $I-$ (or HI); does not form toxic or objectionable compounds with $I_2$; improves the teat appearance; reduces teat callousing and cracking; improves milk let down; reduces discomfort when milking; maintains a suitable capability for reducing the spread of mastitis; has a reasonably good phase stable shelf life over a reasonably wide temperature range; and, is inexpensive to formulate.

THE INVENTION

According to the invention, an iodophor teat dip formulation is provided comprising an emulsifier/dispersant of water soluble, nonionic, fatty alcohol polyglycol ether carboxylic acids; glycerin, and the like; effective amounts of $I_2$ and $I-$ (or HI, and the like); and a pH buffer. A suitable emulsifier/dispersant of this type is sold by Alcolac Inc. under the trade names of AKYPO™RLM-45, AKYPO™RLM-100, AKYPO™RLM-130 and AKYPO™RLM-160, and mixtures thereof, the preferred composition being AKYPO™RLM-100 (Chemical Abstracts Registry 74349-89-6).

As described in "McCutcheon's Emulsifiers & Detergents", 1989, these AKYPO™RLM emulsifiers/dispersants are listed for personal care products to improve skin feel, in high electrolyte household and industrial formulae, and as an emulsifier for synthetic latex, but they are not listed for use in teat dip formulations. The entire contents of "McCutcheon's Emulsifiers & Detergents" 1989-1994 are incorporated herein by reference.

However, according to the invention, it has been discovered unexpectedly that used in conjunction with appropriate amounts of glycerin, an iodophor such as $I_2$ $I-$ (or HI) and, a pH buffer, these water soluble, emulsifiers/dispersants produce a teat dip having the above requisite properties. An adequate, liquid phase stable life over a wide range of ambient temperatures is obtained and moreover, the emulsifier/dispersant probably complexes the iodine and maintains the iodine in solution; this prevents the iodine from precipitating and forming a separate, solid phase. Also, the emulsifier/dispersants function together with the glycerine to impart the necessary emolliency for smooth teats, with reduced cracking, callousing and sores. This lessens the risk of infection sites leading to mastitis, and other diseases.

The AKYPO™RLM emulsifiers/dispersants used in the formulation are laureth/myristic (11–17) carboxylic acids, with an HLB (Hydrophilic/Lipophilic Balance) number of about 10–16; AKYPO™RLM-100 itself has an HLB of 14.8. The formulation may have a small content (e.g., 5%) of stearic acid. Typical formulations comprise $I_2$: about 0.45%–1.3%; HI, or equivalent (e.g., KI, NaI, CaI$_2$, etc., and mixtures thereof): sufficient to form about 0.25%–0.3% I–; glycerin, and the like: about 5%–12.5%; a buffer such as citric acid and/or lactic acid; and, caustic for adjusting the pH to about 4.0–5.5, and preferably to about 4.8–5.2; emulsifier/dispersant: about 7.5%–12.5%; and, water: balance, all parts by weight.

If the glycerin content is below about 5%, the formulation did not appear effective. Other hydroxy equivalents to glycerine may be employed, and include: glycerine; sorbitol; mannitol; galacticol; 1,2,6-hexanetriol; non-ionic polyethylene glycol having a molecular weight of from 100 to 800; the propylene and di-propylene glycols; the pentitols such as arabitol; and, mixtures thereof; however, glycerine is preferred.

If the emulsifier/dispersant content is below about 7.5%, the formulation becomes unstable due to lack of iodine complexing capability, and if the emulsifier/dispersant content is above about 12.5%, no significant improvement was observed.

Using an AKYPO™RLM-100 emulsifier/dispersant of about 10%; an $I_2$ content of about 1.05%; an I– content of about 0.28%; about 10% glycerin; citric acid to buffer the pH; caustic to obtain a pH range of about 4.8–5.2; and the balance water (all parts by weight), a suitable formulation was produced having a phase-stable shelf life of about two (2) years within an ambient temperature range of about 30° F.–110° F. When employed as a bovine teat dip, the formulation may be produced as a concentrate and then diluted with water prior to use.

EXAMPLE 1

Using the above formulation, several herds totalling 2,600 dairy cows was treated during a four month period with about 625,000 teat dips. The herd initially had a low mastitis and infection rate, and use of the above formulation neither improved or worsened the condition of the herd. However, there was a significant improvement in teat appearance, such as a smoother teat, with significantly fewer cracks and a consequent lessened opportunity for spreading an infectious disease such as mastitis. Also there was noted a greater improvement in faster let down and onset of milking, indicating reduced irritation of the cow teats.

The life span of cows is about three to seven years, and during the period commencing from the four month tests in 1988 to 1994, no significant change in the herd life span was noted.

EXAMPLE 2

In a more recent 1994 test, 12 dairy herds of about 200 cows each were treated with the above formulation, and a noticeable improvement in teat condition was observed within about ten (10) days. Fewer cracks, sores, callousing, etc., appeared, resulting in the cow teats being much easier to prepare for milking and a a consequent faster milking operation due to less discomfort.

Also, there was no increase in the somatic (white cell) count, an increase in this cell count being the first sign of a reduced resistance to infectious disease such as mastitis. Additionally, there was a decreased reaction of milker's hands such as chapping, etc., compared to using the NOR-FOX NP-9 nonyl phenoxy surfactant.

The teat dip and method of this invention provides a product having good germicidal properties, and which imparts a smoother teat with fewer callouses, roughness, sores and cracking. Use of the formulation thus reduces entry sites for infection and subsequent spreading of disease, such as mastitis and milking is made easier, due to less teat irritation. Moreover, the teat dip formulation of this invention is relatively inexpensive and has a reasonably good shelf life at ambient conditions.

It has also been found that once the cow teats have been improved to the point where they are in a healthy condition, the teat concentrate may be used at a greater dilution to reduce costs and still maintain their healthy status.

The laureth/myristic surfactant employed in the formulation of this invention may be used in conjunction with $I_2$ and $I^-$ as a concentrate, generally containing: $I^{31}$: 2%–16%; $I_2$: 3%–40%; laureth/myristic surfactant: 50%–95%; and, water: balance, all parts by weight. A preferred concentrate contains: $I^-$: 6.8%; $I_2$: 22%; RLM™100: 66%; and, water: 5.2%, all parts by weight.

This concentrate may then be diluted to produce various skin and body care products for use in a carrier such as commercial liquid soaps, sprays, powders, creams, ointments and mixtures thereof to improve skin smoothness, to reduce chapped, scratched or abraded hands, or rashes; as a surgical scrub; as a skin germicide for cuts, dressings, wounds, etc; for acne treatment; for animal and pet shampoos, etc.

For these uses, the formulation of this invention may include germicides, insect repellents, perfumes, moisturizers, antifungal agents, emollients, humectants, defoamers, antibiotics, additional specific soaps, etc.

In the diluted form, such as in liquid soap, ointment, etc., a typical amount of concentrate at the lower concentration level is about 30 ppm, and at the higher concentration level, the $I_2$ concentration should not exceed about 1.1% by weight. The $I^-$ may be formulated as an ion of Na, K, Mg, Fe, Zn, Mn, Ca, $H^+$, etc.

While acne itself is not considered a serious disease, it does pose psychological problems, and hence any alleviation of acne and/or associated skin scarring effects would be desirable. The above formulation of this invention was tested daily for various periods of time on three subjects, ranging in age from 14 years (female)—test period 1.5 months (applied with a liquid skin care soap); 28 years (male)—test period 1 month (applied as a dilute solution); and, 42 years (female)—test period 9 months (applied with a liquid skin care soap). All three tests resulted in complete acne remission, with mitigation of scarring due to skin peeling.

In a fourth test, a male subject in his mid-fifties washed the back of one hand with the concentrate of this invention, the other hand being used as a control. The daily treatment was designed to remove burn scar tissue, and after 2 months of washing, a slow but noticeable improvement was observed.

The concentrate was formed with a foamer-thickener to produce a 0.75% $I_2$ skin wash.

Additionally, the formulation of this invention may be augment other less expensive teat dips to reduce costs. In this type of usage, about 0.045% by weight of the concentrate is used, the balance being the less expensive teat dip.

The concentrate also may be employed to protect the hands when working with food, and when working with food and medical utensils. Also, the diluted concentrate is useful to protect the hands during contact with sanitizing iodine solutions used for example in conjunction with pet shampoos.

I claim:

1. A teat dip solution, comprising: a water soluble solution of a non-ionic, laureth (11–16) carboxylic acid having an HLB of about 10–16: about 7.5%–12.5%; an effective amount of an iodophor; glycerin, and the like: about 5%–12.5%; a buffer; an agent for adjusting the solution pH to about 4.0–5.5; and, water: balance, all parts by weight.

2. A concentrate solution suitable, by dilution, for skin care and germicide use, comprising: a water soluble solution of a non-ionic, laureth/myristic (11–16) carboxylic acid having an HLB of about 10–16; about 50%–95%; $I^-$: about 2%–16%; $I_2$: 3%–40%; and, water: balance, all parts by weight.

3. The solution of claim 2, admixed with a carrier, the concentrate solution comprising from about 30 ppm concentration in the carrier to about 1.1% $I_2$ concentration in the carrier.

4. The solution of claim 3, comprising: $I^-$: about 6.8%; $I_2$: about 22%; laureth/myristic (11–16) carboxylic acid: about 66%; and, water: about 5.2%, all parts by weight.

5. The solution of claim 3, in which the carrier is selected from the class consisting of liquid soaps, sprays, powders, creams, ointments and mixtures thereof.

6. The solution of claim 3, in which the carrier includes a foamer-thickener.

7. A method for treating acne and scar tissue, comprising applying the solution of claim 3 to the acne and scar tissue.

8. The solution of claim 1, comprising: a water soluble solution of a laureth/myristic (11–16) carboxylic acid having an HLB of about 10–16: about 7.5%–12.5%; an $I_2$ content of about 0.45%–1.3%; HI, or equivalent: sufficient to form about 0.25%–0.3% I–; glycerin, and the like: about 5%–12.5%; a buffer; caustic for adjusting the solution pH to about 4.0–5.5; and, water: balance, all parts by weight.

9. The solution of claim 8, in which the laureth/myristic (11–16) carboxylic acid has an HLB of about 14.8.

10. The solution of claim 2, in which about 0.045% by weight of the concentrate is emplyed to augment a teat dip.

11. The solution of claim 8, which contains glycerine, sorbitol, mannitol, galacticol, the propylene and di-propylene glycols, 1,2,6-hexanetriol, pentitols including arabitol, non-ionic polyethylene glycol having a molecular weight of from 100–800, and mixtures thereof.

12. The solution of claim 8, having a phase stable shelf life of about two years at ambient temperature.

13. The solution of claim 8, comprising a non-ionic, laureth/myristic (11–16) carboxylic acid: about 10%; an $I_2$ content of about 0.25%–0.3%; about 10% glycerin; a pH buffer; caustic to obtain a solution pH range of about 4.0–5.5; and the balance water, all parts by weight.

14. The solution of claim 8, comprising: laureth/myristic (11–16) carboxylic acid with an HLB of 14.8; an I– content of about 0.28%; a buffer of citric or lactic acid; and, caustic to adjust the solution pH to about 4.8–5.2.

15. A method of treatment for teats to reduce the spread of infectious disease, by applying to the teat area a solution, comprising: a water soluble solution of a non-ionic, laureth/myristic (11–16) carboxylic acid having an HLB of about 10–16: about 7.5%–12.5%; an effective amount of an iodophor; glycerine, and the like: about 5%–12.5%; a buffer; a caustic for adjusting the solution pH to about 4.0–5.5; and, water: balance, all parts by weight.

16. The method of claim 15, in which the solution comprises a laureth/myristic (11–16) carboxylic acid having an HLB of about 10–16: about 7.55–12.5%; and $I_2$ content of about 0.45%–1.3%; HI or equivalent: sufficient to form about 0.25%–0.3%I–; glycerin, and the like: about 5%–12.5%; a buffer; caustic for adjusting the solution pH to about 4.0–5.5; and, water: balance, all parts by weight.

17. The method of claim 15, in which the laureth/myristic (11–16) carboxylic acid has an HLB of about 14.8.

18. The method of claim 15, in which the buffer is selected from the class consisting of citric acid, lactic acid and mixtures thereof, and the solution pH is about 4.8–5.2.

19. The method of claim 15, in which the solution comprises a non-ionic laureth/myristic (11–16) carboxylic acid: about 10%; an $I_2$ content of about 0.25%–3.0%; glycerin: about 10%; a pH buffer; caustic to obtain a pH range of about 4.0–5.5; and, the balance water, all parts by weight.

20. A method for treating acne and scar tissue, comprising applying thereto a solution comprising a water soluble solution of a non-ionic, laureth/myristic (11–16) carboxylic acid having an HLB of about 10–16: about 50%–95%; about 30 ppm $I_2$; about 2%–16%; and, water: balance, all parts by weight.

* * * * *